US006831061B2

(12) United States Patent
Lee et al.

(10) Patent No.: US 6,831,061 B2
(45) Date of Patent: Dec. 14, 2004

(54) APICIDIN-DERIVATIVES, THEIR SYNTHETIC METHODS AND ANTI-TUMOR COMPOSITIONS CONTAINING THEM

(75) Inventors: Hyang Woo Lee, 813-1801, Suri Apartment Sanbon-dong, Kyunggi-do Gunpo-si, 435-040 (KR); Young Hoon Jung, 913-501, Jugong Apartment, Burim-dong, Kyunggi-do, Gwachun-si, 427-050 (KR); Jeung Whan Han, 424-1003, Byoksan Apartment, Jungja-dong, Jangan-ku, Kyunggi-do Suwon-si, 440-300 (KR); Seok Yong Lee, 1-51, Sambu Apartment 30-3, Yoido-dong, Yongdeungpo-ku Seoul, 150-794 (KR); Yin Won Lee, 1419-602, Mokdong Apartment, Yangchun-ku, Seoul, 158-702 (KR); Hoi Young Lee, 8-204, LG Apartment Doryong-dong, Yusung-ku, Daejeon, 305-340 (KR)

(73) Assignees: Hyang Woo Lee, Gunpo-si (KR); Young Hoon Jung, Gwanchun-si (KR); Jeung Whan Han, Suwon-si (KR); Seok Yong Lee, Seoul (KR); Yin Won Lee, Seoul (KR); Hoi Young Lee, Daejeon (KR); Ok Pyo Zee, Daejeon (KR)

( * ) Notice: Subject to any disclaimer, the term of this patent is extended or adjusted under 35 U.S.C. 154(b) by 0 days.

(21) Appl. No.: 10/600,392

(22) Filed: Jun. 20, 2003

(65) Prior Publication Data

US 2004/0014647 A1 Jan. 22, 2004

Related U.S. Application Data

(63) Continuation of application No. PCT/KR01/02228, filed on Dec. 21, 2001.

(30) Foreign Application Priority Data

Dec. 22, 2000 (KR) ........................................ 2000/80180

(51) Int. Cl.[7] ........................ A61K 38/00; A61K 31/15; A61K 38/12
(52) U.S. Cl. ........................ 514/10; 514/590; 514/632; 514/639; 514/640; 530/317
(58) Field of Search ........................ 514/10, 590, 639, 514/640; 530/317

(56) References Cited

U.S. PATENT DOCUMENTS 6,649,658 B1 * 11/2003 Corvi Mora et al. ....... 514/640

OTHER PUBLICATIONS

Singh et al, Journal of Organic Chemistry, (2002) 67 (3) 815–825.*
Colleti, et al Bioorganic and Medicinal Chemistry Letters, (2001), 11 (2), 107–111.*

Mou et al., "Synthesis of (S)–2–amino–8–oxodecanoic acid (Aoda) and apicidin A," Tetrahedron Letters 42:6603–6606 (2001).
Murray et al., "The Synthesis of Cyclic Tetrapeptoid Analogues of the Antiprotozoal Natural Product Apicidin," Bioorganic & Medicinal Chemistry Letters 11:773–776 (2001).
Kim et al., "Transcriptional Activation of p21 WAF1/CIP1 by Apicidin, a Novel Histone Deacetylase Inhibitor," Biochemical and Biophysical Research Communications 281:866–871 (2001).
Colletti et al., "Broad Spectrum Antiprotozoal Agents that Inhibit Histone Deacetylase: Structure–Activity Relationships of Apicidin. Part 1," Bioorganic & Medicinal Chemistry Letters 11:107–111 (2001).
Colletti et al., "Broad Spectrum Antiprotozoal Agents that Inhibit Histone Deacetylase: Structure–Activity Relationships of Apicidin. Part 2," Bioorganic & Medicinal Chemistry Letters 11:113–117 (2001).
Colletti et al., "Tryptophan–replacement and indole–modified apicidins: synthesis of potent and selective antiprotozoal agents," Tetrahedron Letters 41:7825–7829 (2000).
Meinke et al., "Synthesis of side chain modified apicidin derivatives: potent mechanism–based histone deacetylase inhibitors," Tetrahedron Letters 41:7831–7835 (2000).
Colletti et al., "Design and synthesis of histone deacetylase inhibitors: the development of apicidin transition state analogs," Tetrahedron Letters 41:7837–7841 (2000).
Kim et al., "Apicidin, an inhibitor of histone deacetylase, prevents H–ras–induced invasive phenotype," Cancer Letters 157:23–30 (2000).
Andrews et al., "Anti–malarial effect of histone deacetylation inhibitors and mammalian tumour cytodifferentiating agents," International Journal for Parasitology 30:761–768 (2000).
Singh et al., "Apicidins: Novel Cyclic Tetrapeptides as Coccidiostats and Antimalarial Agents from Fusarium pallidoroseum," Tetrahedron Letters, 37:45, 8077–8080 (1996).

* cited by examiner

*Primary Examiner*—Christopher R. Tate
*Assistant Examiner*—Edward Ward
(74) *Attorney, Agent, or Firm*—Heslin Rothenberg Farley & Mesiti P.C.

(57) ABSTRACT

A substituted apicidin derivative, a method of synthesis therefore, and an anti-tumor composition comprising the same are disclosed. The substituent of the derivative is preferably semicarbazone, thiosemicarbazone, hydrazone, tert-butylhydrazone, phenylhydrazone, 2,4-dinitrophenylhydrazone, 4-methoxyphenylhydrazone, 3-methoxyphenylhydrazone, 4-nitrophenylhydrazone, benzylhydrazone, methanesulfonylhydrazone, benzenesulfonylhydrazone, 4-methylbenzenesulfonylhydrazone, benzoylhydrazone, 4-nitrobenzoylhydrazone, carbohydrazone, benzyloxime or acetoxime. The compound has strong inhibition effect against histone deacetylase and detransforming activities and specifically inhibit growth of cancer cells. Therefore, it is useful in preparation of an anti-tumor composition.

11 Claims, No Drawings

APICIDIN-DERIVATIVES, THEIR SYNTHETIC METHODS AND ANTI-TUMOR COMPOSITIONS CONTAINING THEM

This application is a continuation of PCT/KR01/02228 filed Dec. 21, 2001.

FIELD OF THE INVENTION

The present invention relates to an apicidin-derivative, a method of synthesis therefore, and an anti-tumor composition containing the same.

BACKGROUND OF THE INVENTION

Histone is a basic protein bonded to DNA in a nucleus of a eukaryotic cell. Nucleosomal core histones undergo reversible acetylation at the amino group of specific lysine residues located in their N-terminal tails. Reversible acetylation of histone is supposed to mediate changes in chromatin structure, which is important in the regulation of gene expression.

The level of acetylation of histone in cell is controlled by equilibrium between the activities of two specific enzymes, histone acetyltransferase and histone deacetylase. So far, it has been reported that inhibitors having various structures inhibit human histone deacetylase.

The inhibitors are classified according to their structure as follows:

1) butyrate having a structure of a fatty acid—See, Newmark, H. L. et al., *Cancer Lett.*, 78:1–5 (1994);
2) tricostatin A, suberoylanilide hydroxamic acid (SAHA) and oxamplatin having a structure of a hydroxamic acid—See, Tsuji, Ni. et al., *J. Antibiot (Tokyo)*, 29:1–6 (1976); Richon. V. M. et al., *Proc. Natl. Acad. Sci. USA*, 95:3003–3007 (1998); and Kim, Y. B. et al., *Oncogene*, 18:2461–2470 (1999);
3) trapoxin A having a cyclic tetrapeptide structure containing 2-amino-8-oxo-9,10-epoxy-decanoyl (AOE)—See, Kijima, M. et al., *J. Biol. Chem.*, 268:22429–22435 (1993);
4) FR901228 and apicidin having a cyclic tetrapeptide structure without containing AOE —See, Nakajima, H. et al., *Exp. Cell. Res.*, 241:126–133 (1998); Darkin-Rattray, S. J. et al., *Proc. Natl. Acad. Sci. USA*, 93: 13143–13147, 1996); and
5) MS-27-275 having a benzamide structure—See, Saito, A. et al., *Proc Natl. Acad. Sci. USA*, 96:45924597 (1999).

These compounds are known to inhibit the histone deacetylase in human cells, growth of cancer cells, and growth of tumors in animal models. Among them, the only compound which has received clinical approval and has been widely used is butyrate. However, the butyrate compound should be used at a high concentration (in a level of mM) so as to inhibit the histone deacetylase, and has a tendency to activate enzymes other than the histone deacetylase. Thus, this compound cannot be said to be an ideal agent. Clinical researches for a compound of a different structure which can selectively inhibit histone deacetylase at a low concentration (in a level of μM (micromolar)) are actively conducted. FR901228 is currently under clinical trial (phase I, National Cancer Institute).

Based on the above-described facts, the histone deacetylase inhibitors are believed to be highly probable candidates which can be developed as agents having inhibitory effects against growth of tumors. However, at the present, use of these inhibitors in preparation of anti-cancer agents and their functional mechanisms are still not known.

The present inventors synthesized various derivatives from apicidin as a core molecule and filed an application for patent as to three compounds, SD9801, SD9802, and SD9803, which are each capable of inhibiting effectively growth of cancer cells (Korean Application for Patent No. 1999-11883).

Thereafter, the present inventors steadily endeavored to conduct research on histone deacetylase and finally discovered an apicidin derivative having excellent inhibitory effect against histone deacetylase at a low concentration, detransforming activity, and also being able to specifically inhibit growth of cancer cells while showing substantially no toxicity to normal cells. The present invention is formed based on this discovery.

Therefore, it is an object of the present invention to provide an apicidin derivative having a low toxicity to normal cells, a method of synthesis therefore, and an anti-tumor composition containing the same.

SUMMARY OF THE INVENTION

The present invention relates to an apicidin derivative represented by the following formula 1:

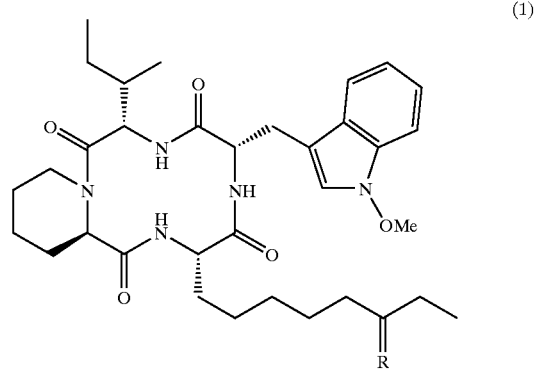

(1)

wherein:

R is chosen from semicarbazone, thiosemicarbazone, hydrazone, tert-butylhydrazone, phenylhydrazone, 2,4-dinitrophenylhydrazone, 4-methoxyphenylhydrazone, 3-methoxyphenylhydrazone, 4-nitrophenylhydrazone, benzylhydrazone, methanesulfonylhydrazone, benzenesulfonylhydrazone, 4-methylbenzenesulfonylhydrazone, benzoylhydrazone, 4-nitrobenzoylhydrazone, carbohydrazone, benzyloxime or acetoxime.

Also, the present invention relates to a method for producing an apicidin derivative of the formula 1 characterized by reacting apicidin represented by the following formula 2 with hydrazines, carbazides or amines in the presence of a base or acid, as shown in the following reaction scheme 1.

Scheme 1

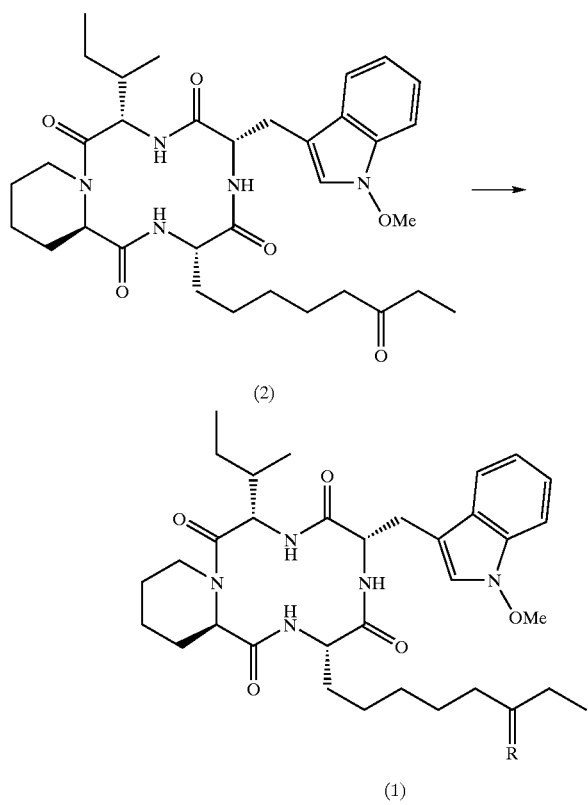

Here, as a reaction solvent for the above reaction, alcohols such as methanol or ethanol; aromatic solvents such as benzene or toluene; tetrahydrofuran (THF); ether and the like may be preferably used. More preferably, methanol or ethanol may be used. The base which can be used in the above reaction is preferably triethylamine, pyridine, sodium acetate and the like, more preferably triethylamine or pyridine. The acid which can be used in the above reaction is preferably acetic acid, hydrochloric acid or sulfuric acid in a small amount, more preferably acetic acid. In addition, the reaction scheme may further comprise a separation process by subjecting the reaction mixture to a reduced pressure to remove the reaction solvent and separating further using a commonly known method.

Also, in another aspect of the present invention, there is provided a histone deacetylase inhibitor containing a compound of the formula 1.

In a further aspect of the present invention, there is provided an anti-tumor composition comprising a compound of the formula 1 as an active ingredient.

The anti-tumor composition comprising a compound of the formula 1 as an active ingredient according to the present invention may be combined with a pharmaceutically acceptable carrier and may be applied in a form of injection solution for parenteral administration, oral administration, a liquid formulation such as syrup or emulsion, solid formulation such as tablets, capsules, granules or powders, and a topical formulation such as ointments.

Examples of the carrier for oral administration may include preferably starch, mannitol, cellulose, water or ethyl alcohol. Examples of the carrier for injection may include preferably water, physiological saline or dextrose solution. The anti-tumor composition according to the present invention may be combined with a carrier in a ratio of 1:99 to 99:1 by weight respective to the active ingredient.

In a still further aspect of the present invention, there is provided a method for treating or preventing tumors comprising administrating a therapeutically effective amount of a compound of the formula 1.

In a still further aspect of the present invention, there is provided use of a compound of the formula 1 as an anti-tumor agent.

DETAILED DESCRIPTION OF THE INVENTION

Now, the present invention will be described in detail using the following examples examples, but it should be understood that the present invention is not limited thereto.

EXAMPLE 1

Synthesis of Semicarbazone Derivative of Apicidin

Separation of Apicidin

A sample of beans harvested in 1997 was cultured in a potato dextrose agar (PDA) slant culture for 5 days. The produced mycelia were collected and cut. The mycelia segments were separated off and purified. The mycelia segments thus obtained were preserved at about 15° C. along with soil which had been subjected to a sterilization treatment, until used in this example.

Total 1.6 kg of wheat as a medium was divided into eight 1 L-Erlenmeyer flasks, each containing 200 g. 120 mL of distilled water was added to the flasks. The flasks were vacuum sterilized twice for 1 hour at 121° C. at 24 hours intervals and used as a medium.

The mycelia which had been removed from the potato dextrose agar culture at 5 days after inoculation were inoculated into the sterilized wheat medium. The mycelia were cultured for 4 weeks at 25° C. After culturing, the wheat medium was removed from the flask, dried in a hood at between 22 and 24° C. for about 5 days and finely ground. The ground medium was preserved at −15° C. until use.

Total 1.6 kg of ground wheat medium was divided into 5 L flasks with each containing 500 g, extracted three times with 15 L of ethyl acetate, filtered using Whatman No. 2 filter paper and condensed under reduced pressure. The condensed extract was dissolved in 200 mL of distilled water and separated on a column (5.5 cm inner diameter) packed with 1 kg of amberlite XAD-2. The product was washed with total 6 L of distilled water, eluted with 6 L of methanol and condensed under reduced pressure. The methanol extract was dissolved in ethyl acetate and separated on a column (5 cm inner diameter) packed with 500 g of florisil. Here, the eluent solvent used was a mixture of ethylacetate and n-hexane (3:1 v/v).

The F2 fraction wherein cyclic tetrapeptide (apicidin) was contained was identified using thin layer chromatography (TLC) and continuously separated. The F2 fraction was dissolved in a small amount of chloroform and finally separated on a chromatotron using silica gel with particle size of 2 to 25 μm (Merck) containing a fluorescence indicator and a petroleum binder, and a glass plate having a thickness of 2 mm. As the eluent solvent, chloroform-methanol (97:3, v/v) was used at a flow rate of 8 mL/min. During the separation on the chromatotron, apicidin was monitored with ultraviolet light at a wavelength of 254 nm. The purity of the separated apicidin was confirmed using thin layer chromatography. Here, p-anisaldehyde was used as a coloring agent.

Following the above-described method, about 800 mg of pure apicidin was obtained as white powders. The purity of the resulting apicidin was confirmed by thin layer chromatography, wherein only one violet spot was observed, which indicates that the product was highly pure.

Synthesis of Semicarbazone Derivative of Apicidin 700 mg (1.11 mmol) of apicidin separated in Example 1.1 was dissolved in 300 mL of methanol. 491 mg (4.44 mmol) of semicarbazide hydrochloride and 443.8 mg (4.44 mmol) of TEA were added to the solution, followed by refluxing for 12 hours. After removing the reaction solvent under reduced pressure, the residue was dissolved in 500 mL of methylene chloride. The resulting solution was washed with 300 mL of 1N sodium bicarbonate, 300 mL of 1N citric acid and 300 mL of brine in order, dried over anhydrous magnesium sulfate, condensed under reduced pressure, and purified by column chromatography (ethylacetate; $CHCl_3:MeOH=10:1$). 653.8 mg (85.3%) of the pure titled compound was obtained while 92.8 mg (12.1%) of the starting material was recovered.

Rf0.45 ($CHCl_3:MeOH=10:1$)

$^1$H-NMR (500 MHz, DMSO)

δ 9.02 (s, 1H), 7.84 (d, 1H, J=9.5 Hz), 7.60 (d, 1H, J=8.0 Hz), 7.49 (d, 1H, J=9.5 Hz), 7.41 (t, 2H, J=7.5 Hz), 7.20 (d, 1H, J=4.0 Hz), 7.07 (d, 1H, J=7 Hz), 6.16 (s, 2H), 6.12 (d, 1H, J=10.5 Hz), 5.16 (d, 1H, J=5 Hz), 4.55 (t, 1H, J=20 Hz), 4.33 (m, 1H), 4.19 (m, 1H), 4.01 (s, 3H), 3.97 (s, 1H), 3.75 (d, 1H, J=8.0 Hz), 3.07 (t, 1H, J=23.5 Hz), 3.02 (t, 1H, 14.5 Hz), 2.39–2.31 (m, 1H), 1.95 (d, 2H, J=10.5 Hz), 1.81 (d, 1H, J=13.5 Hz), 1.62–1.49 (m, 7H), 1.35–1.07 (m, 11H), 1.01–0.98 (m, 3H), 0.94–0.81 (m, 3H)

EXAMPLE 2

Synthesis of Hydrazone Derivative of Apicidin 10.0 mg (0.016 mmol) of apicidin separated in Example 1.1 was dissolved in 5.0 mL of methanol. 5.0 mg (0.048 mmol) of hydrazine dihydrochloride and 9.8 mg (0.096 mmol) of TEA were added to the solution, followed by refluxing for 5 hours. After removing the reaction solvent under reduced pressure, the residue was dissolved in 10 mL of methylene chloride. The resulting solution was washed with 5 mL of 1N sodium bicarbonate, 5 mL of 1N citric acid and 10 mL of brine in order, dried over anhydrous magnesium sulfate, condensed under reduced pressure, and purified by column chromatography ($CHCl_3:MeOH=20:1$). 4.5 mg (44.1%) of the pure titled compound was obtained.

Rf 0.21 ($CHCl_3:MeOH=20:1$)

$^1$H-NMR (500 MHz, DMSO)

δ 7.84 (d, 1H, J=9.5 Hz), 7.60 (m, 3H), 7.49 (d, 1H, J=9.5 Hz), 7.41 (t, 2H, J=7.5 Hz), 7.20 (d, 1H, J=4.0 Hz), 7.07 (d, 1H, 7 Hz), 6.16 (s, 2H), 6.12 (d, 1H, J=10.5 Hz), 5.16 (d, 1H, J=5 Hz), 4.55 (t, 1H, J=20 Hz), 4.33 (m, 1H), 4.19 (m, 1H), 4.01 (s, 3H), 3.97 (s, 1H), 3.75 (d, 1H, J=8.0 Hz), 3.07 (t, 1H, J=23.5 Hz), 3.02 (t, 1H, J=14.5 Hz), 2.39–2.31 (m, 1H), 1.95 (d, 2H, J=10.5 Hz), 1.81 (d, 1H, J=13.5 Hz), 1.62–1.49 (m, 7H), 1.35–1.07 (m, 11H), 1.01–0.98 (m, 3H), 0.94–0.81 (m, 3H)

EXAMPLE 3

Synthesis of tert-butylhydrazone Derivative of Apicidin 11.0 mg (0.0176 mmol) of apicidin was dissolved in 5.0 mL of methanol. 6.6 mg (0.0528 mmol) of tert-butylhydrazine hydrochloride and 5.3 mg (0.0528 mmol) of TEA were added to the solution, followed by refluxing for 6 hours. After removing the reaction solvent under reduced pressure, the residue was dissolved in 10 mL of methylene chloride. The resulting solution was washed with 5 mL of 1N sodium bicarbonate, 5 mL of 1N citric acid and 10 mL of brine in order, dried over anhydrous magnesium sulfate, condensed under reduced pressure, and purified by column chromatography ($CHCl_3:MeOH=20:1$). 6.8 mg (55.7%) of the pure titled compound was obtained.

Rf0.31 ($CHCl_3:MeOH=20:1$)

$^1$H-NMR (500 MHz, DMSO)

δ 7.84 (d, 11H, J=9.5 Hz), 7.60 (m, 2H), 7.49 (d, 1H, J=9.5 Hz), 7.41 (t, 2H, J=7.5 Hz), 7.20 (d, 1H, J=4.0 Hz), 7.07 (d, 1H, J=7 Hz), 6.16 (s, 2H), 6.12 (d, 1H, J=10.5 Hz), 5.16 (d, 1H, J=5 Hz), 4.55 (t, 1H, J=20 Hz), 4.33 (m, 1H), 4.19 (m, 1H), 4.01 (s, 3H), 3.97 (s, 1H), 3.75 (d, 1H, J=8.0 Hz),:3.07 (t, 1H, J=23.5 Hz), 3.02 (t, 1H, 14.5 Hz), 2.39–2.31 (m, 1H), 1.95 (d, 2H, J=10.5 Hz), 1.81 (d, 1H, J=13.5 Hz), 1.62–1.49 (m, 7H), 1.37–1.32 (m, 4H), 1.31–1.23 (m, 9H), 1.17–1.03 (m, 6H), 0.97–0.81 (m, 3H)

EXAMPLE 4

Synthesis of Carbohydrazone Derivative of Apicidin 30 mg (0.048 mmol) of apicidin was dissolved in 5.0 mL of methanol. 13 mg (0.144 mmol) of carbohydrazide and 29 mg (0.289 mmol) of TEA were added to the solution, followed by refluxing for 4 hours. After removing the reaction solvent under reduced pressure, the residue was dissolved in 20 mL of methylene chloride. The resulting solution was washed with 10.0 mL of 1N sodium bicarbonate, 10.0 mL of 1N citric acid and 10.0 mL of brine in order, dried over anhydrous magnesium sulfate, condensed under reduced pressure, and purified by column chromatography (ethylacetate; $CHCl_3:MeOH=10:1$). 30.18 mg (90.1%) of the pure titled compound was obtained as white solids.

Rf0.32 ($CHCl_3:MeOH=10:1$)

$^1$H-NMR (500 MHz, DMSO)

δ 9.41 (s, 1H), 9.19 (t, 1H, J=18.5 Hz), 7.83 (t, 1H, J=2.5 Hz), 7.60 (t, 1H, J=5 Hz), 7.54–7.48 (m, 1H), 7.43–7.38 (m, 3H), 7.19 (d, 1H, J=5 Hz), 7.07 (t, 1H, J=7.5 Hz), 6.13 (d, 1H, J=10 Hz), 5.16 (s, 1H), 4.54 (s, 1H), 4.32 (d, 1H, J=5 Hz), 4.23 (t, 1H, J=5 Hz), 4.02 (s, 3H), 3.99 (s, 1H), 3.75 (d, 1H, J=10 Hz), 3.07 (t, 1H, J=10 Hz), 3.02 (t, 1H, J=7.5 Hz), 2.22–2.14 (m, 5H), 1.99–1.90 (m, 2H), 1.80 (d, 2H, J=1.5 Hz), 1.51–1.47 (m, 4H), 1.23–1.14 (m, 12H), 1.04–0.98 (m, 3H), 0.90–0.823 (m, 6H)

EXAMPLE 5

Synthesis of Benzyloxime Derivative of Apicidin 25 mg (0.04 mmol) of apicidin was dissolved in 10 mL of methanol. 7.66 mg (0.048 mmol) of benzyloxyamine hydrochloride and 15.8 mg (0.20 mmol) of pyridine were added to the solution, followed by stirring for 4 hours at room temperature. After removing the reaction solvent under reduced pressure, the residue was dissolved in 15.0 mL of methylene chloride. The resulting solution was washed with 10.0 mL of 1N sodium bicarbonate, 10.0 mL of 1N citric acid and 10.0 mL of brine in order, dried over anhydrous magnesium sulfate, condensed under reduced pressure, and purified by column chromatography (ethylacetate; $CHCl_3:MeOH=10:1$). 25 mg (87.4%) of the pure titled compound was obtained as white solids.

Rf0.48 ($CHCl_3:MeOH=10:1$)

$^1$H-NMR (500 MHz, DMSO)

δ 7.82 (d, 1H, J=10 Hz), 7.61 (d, 1H, J=5 Hz), 7.48 (d, 1H, J=10 Hz), 7.40 (t, 1H, J=5 Hz), 7.33 (t, 5H, f-5 Hz) 7.17 (t, 1H, J=5 Hz), 7.06 (t, 1H, J=5 Hz), 6.12 (d, 1H, J=10 Hz), 5.16 (d, 1H, J=5 Hz), 4.99 (d, 2H, J=5 Hz), 4.54 (t, 1H, J=10

Hz), 4.32 (d, 1H, J=5 Hz), 4.20 (t, 1H, J=7.5 Hz), 3.99 (s, 3H), 3.97 (s, 1H), 3.76 (d, 1H, J=15 Hz), 3.10 (t, 1H, J=7.5 Hz), 3.04 (t, 1H, J=10 Hz), 2.26–2.05 (m, 1H), 1.96 (d, 2H, J=12.5 Hz), 1.81 (d, 1H, J=15 Hz), 1.51–1.46 (m, 7H), 1.35–1.15 (m, 11H), 1.09–0.98 (m, 3H), 0.83–0.82 (m, 3H)

EXAMPLE 6

Synthesis of Acetoxime Derivative of Apicidin

Synthesis of Oxime Derivative of Apicidin 25 mg (0.04 mmol) of apicidin was dissolved in 10 mL of methanol. 3.34 mg (0.048 mmol) of hydroxylamine hydrochloride and 15.8 mg (0.20 mmol) of pyridine were added to the solution, followed by stirring for 4 hours at room temperature. After removing the reaction solvent under reduced pressure, the residue was dissolved in 15.0 mL of methylene chloride. The resulting solution was washed with 10.0 mL of 1N sodium bicarbonate, 10.0 mL of 1N citric acid and 10.0 mL of brine in order, dried over anhydrous magnesium sulfate, condensed under reduced pressure, and purified by column chromatography (ethylacetate; $CHCl_3:MeOH=10:1$). 25.1 mg (98%) of the pure titled compound was obtained as white solids.

Rf0.19 ($CHCl_3:MeOH=10:1$)

$^1$H-NMR (500 MHz, DMSO)

δ 10.18 (d, 1H, J=15 Hz), 7.83 (d, 1H, J=10 Hz), 7.60 (d, 1H, J=10 Hz), 7.49 (d, 1H, J=10 Hz), 7.40 (t, 1H, J=5 Hz), 7.21 (t, 1H, J=7.5 Hz), 7.07 (t, 1H, J=5 Hz), 6.13 (d, 1H, J=10 Hz), 5.17 (d, 1H, J=5 Hz), 4.54 (t, 1H, J=10 Hz), 4.32 (t, 1H, J=5 Hz), 4.22 (t, 1H, J=7.5 Hz), 4.01 (s, 3H), 4.00 (s, 1H), 3.75 (d, 1H, J=15 Hz), 3.10 (t, 1H, J=7.5 Hz), 3.04 (t, 1H, J=10 Hz), 2.20–2.09 (m, 1H), 1.94 (d, 2H, J=15 Hz), 1.81 (d, 1H, J=15 Hz), 1.52–1.48 (m, 7H), 1.0–0.85 (m, 3H), 0.88–0.82 (m, 3H)

Synthesis of Acetoxime Derivative of Apicidin 18 mg (0.028 mmol) of the oxime derivative synthesized above was dissolved in 5 mL of methylene chloride. 3.45 mg (0.034 mmol) of $AC_2O$, 2.67 mg (0.034 mmol) of pyridine and 3.45 mg (0.0282 mmol) of DMAP were added to the solution in order, followed by stirring for 4 hours at room temperature. Upon completion of the reaction, methylene chloride was extracted with water, washed with 20 mL of brine, dried over anhydrous magnesium sulfate, condensed under reduced pressure, and purified by column chromatography (ethylacetate; $CHCl_3:MeOH=10:1$). 1.6 mg (83%) of the pure titled compound was obtained as white solids.

Rf0.41 ($CHCl_3:MeOH=10:1$)

$^1$H-NMR (500 MHz, DMSO)

δ 7.84 (t, 1H, J=5 Hz), 7.60 (d, 1H, 8 Hz), 7.49 (d, 1H, J=10 Hz), 7.40 (t, 1H, J=6 Hz), 7.19 (t, 1H, J=5 Hz), 7.06 (t, 1H, J=5 Hz), 6.13 (d, 1H, J=10 Hz), 5.17 (d, 1H, J=5 Hz), 4.53 (t, 1H, J=10 Hz), 4.32 (t, 1H, J=5 Hz), 4.20 (t, 1H, J=7.5 Hz), 3.76 (d, 1H, J=10 Hz), 3.10 (t, 1H, J=10 Hz), 3.04 (t, 1H, J=7.5 Hz), 2.30–2.20 (m, 1H), 2.08 (d, 3H, J=13 Hz), 1.92 (d, 1H, J=10 Hz), 1.81 (d, 1H, J=15 Hz), 1.50–1.46 (m, 7H), 1.34–1.13 (m, 1H), 1.10–1.00 (m, 3H), 0.87–0.80 (m, 3H)

TEST EXAMPLE 1

Cell Growth Inhibition Assay (SRB Assay)

Cell Culture

HeLa (human cervical cancer cell line), v-ras-transformed NIH3T3 (mouse fibroblast cell line), Colon 3.1-M26 (mouse colon cancer cell line), MG63 (human osteosarcoma cell line) and MCF-7 (human breast cancer cell line) cells were cultured in DMEM (Dulbecco's modified Eagle's medium, produced by Life Technologies, Inc.). A2058 (human melanoma cell line), AGS (human gastric adenocarcinoma cell line), HBL-100 (human breast cancer cell line), CCD-18Co (human normal colon cell line) and LL86 (human normal lung cell line) cells were cultured in RPMI 1640 (Life Technologies, Inc.) in the presence of 10% FBS and 1% penicillin/streptomycin.

After treatment with chemicals, the cells were washed with a buffer (50 mM Tris-HCl, pH 7.5), 120 mM NaCl, 20 mM NaF, 1 mM EDTA, 5 mM EGTA, 15 mM sodium pyrophosphate, 30 mM p-nitrophenyl phosphate, 1 mM benzamidine and 0.1 mM phenylmethylsulfonyl fluoride, and extracted with a buffer (including 1% Nonidet P40). Protein amount was measured according to Bradford method using BSA as a reference. The cell extracts were kept in liquid nitrogen before testing.

Measurement of Cell Growth Inhibition

A cell growth inhibition assay according to sulforhodamine B (SRB) protein dye assay was carried out to examine the effects of apicidin derivative prepared in the Examples on mouse and human cancer cells. The cells were placed in wells and during cultivation were treated with 0.01, 0.1, 0.5, 1, and 2 µg/mL of apicidin, SD9801, SD9802, SD9803, the compound of Example 1, the compound of Example 2 and the compound of Example 3.

After 48 hours of cultivation, the media were removed from the well plates. The cells were fixed with 1 mL of 10% trichloroacetic acid at 4° C. washed 5 times with distilled water and completely dried in the air. The wells were treated with 0.4% SRB solution and died for 30 minutes at an ambient temperature. Subsequently, the wells were washed 5 times with distilled water and dried for 18 hours. To the respective wells, Tris-HCl (1 mL, 10 mM) was added to dissolve the proteins bonded to SRB. The contents of each well were removed and measured for their absorption at 490 nm.

The results are shown in the following Table 1 (EL 808 ultra microplate reader, Bio-Tek instruments, Inc., Winooski, Vt.).

TABLE 1

Growth inhibition against various cancer cells

| | Cell Strain | Growth inhibition $IC_{50}$ (µg/mL) | | | | | | |
|---|---|---|---|---|---|---|---|---|
| | | Apicidin | SD9801 | SD9802 | SD9803 | Example 1 | Example 2 | Example 3 |
| Normal | CCD-18Co | 2.36 | 13.25 | 15.23 | 14.13 | 11.81 | 8.51 | 4.27 |
| | LL86 | 4.25 | 18.55 | 19.32 | 17.33 | 18.25 | 16.33 | 14.76 |

TABLE 1-continued

Growth inhibition against various cancer cells

| | | Growth inhibition $IC_{50}$ (μg/mL) | | | | | | |
|---|---|---|---|---|---|---|---|---|
| | Cell Strain | Apicidin | SD9801 | SD9802 | SD9803 | Example 1 | Example 2 | Example 3 |
| Cancer | v-ras-transformed NIH3T3 | 0.18 | 1.62 | 2.30 | 1.98 | 0.12 | 0.15 | 0.17 |
| | AGS | 0.13 | 1.24 | 1.50 | 1.93 | 0.11 | 0.16 | 0.16 |
| | A2058 | 0.55 | 4.33 | 3.89 | 3.55 | 0.34 | 0.63 | 1.03 |
| | HBL-100 | 0.57 | 3.81 | 3.64 | 3.93 | 0.11 | 0.13 | 0.15 |
| | MCF-7 | 1.17 | 8.45 | 7.04 | 7.87 | 0.82 | 1.03 | 1.01 |
| | HeLa | 0.51 | 3.56 | 2.57 | 2.90 | 0.47 | 0.63 | 0.79 |
| | MG63 | 1.88 | 10.45 | 9.63 | 11.78 | 1.05 | 1.39 | 2.07 |
| | Colon 3.1-M26 | 0.17 | 1.86 | 1.59 | 1.97 | 0.20 | 0.20 | 0.21 |

The absorbance was proportional to the number of cells attached to the well. Thus, the absorbance data from the SRB assay show that the compounds according to the present invention have cell growth inhibition effects against various mouse and human cancer cells.

As seen from the Table 1, the cell growth was significantly inhibited by the apicidin derivatives (Examples 1, 2 and 3) at a very low concentration (μM(micromolar)). In particular, they showed very strong inhibition against AGS, HBL-100 and v-ras-transformed NIH3T3 ($IC_{50}$, below 0.2 μg(microgram)/mL) and moderate inhibition against A2058, MCF7, HeLa, MG63 and Colon 3.1-M26 cells ($IC_{50}$, 0.20 to 2.07 μg(microgram)/mL).

The inhibitions of the apicidin derivatives against cancer cell growth were comparable to that of the core compound, apicidin. However, the derivatives (Example 1, 2 and 3) show very low inhibition against growth of normal cells such as CCD-18Co and LL86 cells, as compared to the cancer cells ($IC_{50}$, 4.27 to 18.25 μg(microgram)/mL). That is, the derivatives (Example 1, 2 and 3) show cell growth inhibitory effect at about 1.8 to 5 times higher concentration for CCD-18Co (human normal colon cells) and about 3.5 to 4.3 times higher concentration for LL86 (human normal lung cells) as compared to apicidin.

Thus, it is noted that the derivatives (Example 1, 2 and 3) show low inhibitory effects on the growth of normal cells and have specific growth inhibition effects against cancer cells. Particularly, the derivative of Example 1 was found to be the safest to normal cells.

Therefore, it was demonstrated that the apicidin derivatives according to the present invention (Example 1, 2 and 3) have strong cell growth inhibition effects against cancer cells at a low concentration while having substantially no toxicity to normal cells at that concentration. Moreover, the compound of Example 1 shows about 5 times higher safety against normal cell growth than the parent compound, apicidin. Meanwhile, the conventional compounds, SD9801, SD9802 and SD9803 filed in Korean Application for Patent No. 1999-11883 show comparable inhibition effects against normal cell growth to the compounds of Examples 1, 2 and 3, but their inhibitory effects against cancer cell growth are much lower than those of the compounds of Examples 1, 2 and 3.

TEST EXAMPLE 2

Examination of Detransforming Activity of Histone Deacetylase

This example was carried out to examine whether the novel apicidin derivatives according to the present invention may induce the detransforming activity which are commonly induced by treatment with histone deacetylase inhibitor. HeLa cells were treated with 0.01, 0.1, 0.5, 1, and 2 μg(microgram)/mL of apicidin, SD9801, SD9802, SD9803, the compound of Example 1, the compound of Example 2, the compound of Example 3 and the compound of Example 4 for 24 hours.

After treatment, the cancer cells were observed using an optical microscope to determine if the shape of the cancer cells was changed to the shape of normal cells, that is, if the derivatives have detransforming activity.

As a result, it is observed that HeLa cells having oval or polygonal shape were changed to a characteristic shape of their normal cells, i.e. a flattened body having filamentous protrusions. The results are shown in Table 2 below

TABLE 2

| Concentration | Detransforming activity | | | | | | | |
|---|---|---|---|---|---|---|---|---|
| (μg/mL) | Apicidin | SD9801 | SD9802 | SD9803 | Example 1 | Example 2 | Example 3 | Example 4 |
| 0 | − | − | − | − | − | − | − | − |
| 0.01 | − | − | − | − | − | − | − | − |
| 0.1 | − | − | − | − | + | + | + | − |
| 0.5 | + | − | − | − | ++ | ++ | ++ | + |
| 1 | ++ | − | − | − | +++ | +++ | +++ | ++ |
| 2 | +++ | + | + | + | ++++ | ++++ | ++++ | +++ |
| 10 | ++++ | ++ | ++ | ++ | ++++ | ++++ | ++++ | ++++ |

As seen from the Table 2, the derivatives from Examples 1, 2, 3 and 4 show detransforming activities comparable to that of the core compound, apicidin. However, the conventional compounds, SD9801, SD9802 and SD9803 filed in Korean Application for Patent No. 1999-11883 show detransforming effects at about 200 times higher concentration compared to apicidin and the compounds of Examples 1, 2, 3 and 4.

TEST EXAMPLE 3

In Vitro Histone Deacetylation Assay

This example was carried out to examine the inhibitory effects of the derivatives of Examples 1, 2, 3 and 4 against histone deacetylase in order to confirm that the high inhibitory effects of the compounds according to the present invention against cancer cell growth are due to inhibition of histone deacetylase.

Histone deacetylase was purified from HeLa cells. The activity of histone deacetylase was measured according to a method known in the art—See, e.g., Inoue, A. et al., *Biochem. Biophys. Acta.*, 20:307–316 (1970). Here, histone with [$^3$H]acetyl group labeled with radio-active materials was used as a substrate for measurement of activity of histone deacetylase. After incubation at 37° C. for 20 minutes, [$^3$H]acetic acid released into medium was extracted with ethylacetate and quantified using a liquid radiation detection method. The results are shown in Table 3 below.

TABLE 3

Histone deacetylase inhibition

| Compound | Histone deacetylase inhibition IC$_{50}$ (nM) |
| --- | --- |
| Apicidin | 5 |
| SD9801 | 1026 |
| SD9802 | 789 |
| SD9803 | 929 |
| Example 1 | 1 |
| Example 2 | 3 |
| Example 3 | 25 |
| Example 4 | 39 |

As seen from the Table 3, the compounds according to the present invention inhibit histone deacetylase in a concentration-dependent manner. In particular, taking it into considerations that the compounds of Example 1 and 2 at concentrations of 1 and 3 nM, greater inhibitory effect on the activity of histone deacetylase than their parent compound, apicidin (IC$_{50}$, 5 nM). The conventional compounds, SD9801, SD9802 and SD9803 filed in Korean Application for Patent No. 1999-11883 show about 24 to 1000 times lower inhibitory effect on histone deacetylase activity compared to apicidin and the compounds of Examples 1, 2, 3 and 4.

Summarizing the results of the above Examples together, the apicidin derivatives (Examples 1, 2 and 3) according to the present invention have superior inhibition strength against histone deacetylase, detransforming activities and inhibition effects against cancer cells compared to the parent compound, apicidin while having a very weak toxicity to normal cells.

Considering such effects of the compounds of the present invention are intimately associated with inhibition strength against histone deacetylase in vivo and the compounds have low inhibitory effects on the growth of normal cells, it is concluded that the compounds of the present invention can inhibit growth of cancer cells more selectively than apicidin and the conventionally filed compounds (SD9801, SD9802 and SD9803; Korean Application for Patent No. 1999-11883).

As described above, the compounds according to the present invention at their low concentration can strongly inhibit histone deacetylase, have detransforming activities and specifically inhibit growth of cancer cells. Also, the compounds show substantially no toxicity to normal cells at their effective concentration to inhibit growth of cancer cell. Thus, the compounds are selective inhibitor which can inhibit growth of cancer cells by suppressing histone deacetylase and hence, can provide superior anti-tumor composition with a low toxicity to normal cells.

CROSS REFERENCE TO RELATED APPLICATION AND CLAIM FOR FOREIGN PRIORITY

This application is a continuation of PCT/KR01/02228, filed Dec. 21, 2001 and claims priority from KR 2000-80180, filed Dec. 22, 2000. The entire content of the earlier applications is incorporated by reference.

We claim:

1. A method of the formula 1:

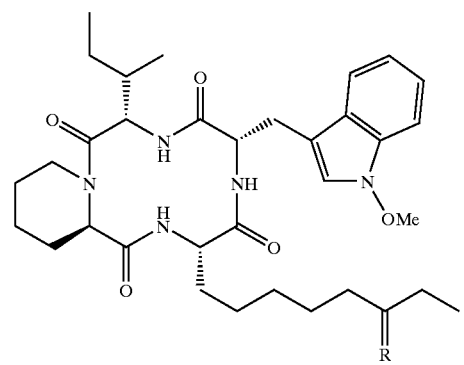

(1)

wherein R is chosen from semicarbazone, thiosemicarbazone, hydrazone, tert-butylhydrazone, phenylhydrazone, 2,4-dinitrophenylhydrazone, 4-methoxyphenylhydrazone, 3-methoxyphenylhydrazone, 4-nitrophenylhydrazone, benzylhydrazone, methanesulfonylhydrazone, benzenesulfonylhydrazone, 4-methylbenzenesulfonylhydrazone, benzoylhydrazone, 4-nitrobenzoylhydrazone, carbohydrazone, benzyloxime and acetoxime.

2. The compound of claim 1, wherein R is chosen from semicarbazone, hydrazone, tert-butylhydrazone, carbohydrazone, benzyloxime or acetoxime.

3. A histone deacetylase inhibitor comprising a compound according to claim 1.

4. An anti-tumor composition comprising a compound according to claim 1.

5. A method for treating tumors and/or reducing the risk thereof comprising administering to a subject in need thereof a therapeutically effective amount of a compound according to claim 1.

6. A method for producing a compound according to claim 1, wherein the method comprises the step of reacting apicidin (represented by formula 2):

(2)

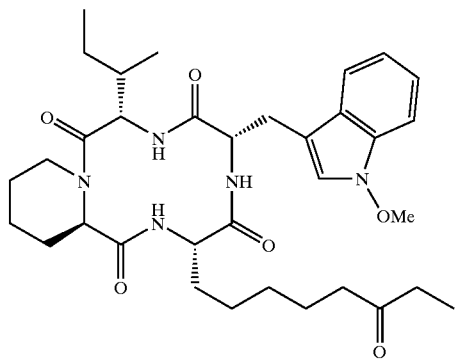

with a hydrazine, carbazide or an amine, in the presence of an acid or a base.

7. The method of claim 6, wherein the step of reacting apicidin with the chosen compound involves the use of methanol or ethanol as a reaction solvent.

8. The method of claim 6, wherein the base is chosen from triethylamine or pyridine.

9. The method of claim 6, wherein the acid is acetic acid.

10. The method of claim 7, wherein the base is chosen from triethylamine or pyridine.

11. The method of claim 7, wherein the acid is acetic acid.

* * * * *

UNITED STATES PATENT AND TRADEMARK OFFICE
CERTIFICATE OF CORRECTION

PATENT NO. : 6,831,061 B2
DATED : December 14, 2004
INVENTOR(S) : Lee et al.

It is certified that error appears in the above-identified patent and that said Letters Patent is hereby corrected as shown below:

Title page,
Item [73], Assignee, delete "Young Hoon Jung, Gwanchun-si (KR)" and insert -- Young Hoon Jung, Gwachun-si (KR) --

Column 12,
Line 22, delete the word "method" and insert -- compound --

Signed and Sealed this

Twenty-sixth Day of April, 2005

JON W. DUDAS
*Director of the United States Patent and Trademark Office*